Figure 1:
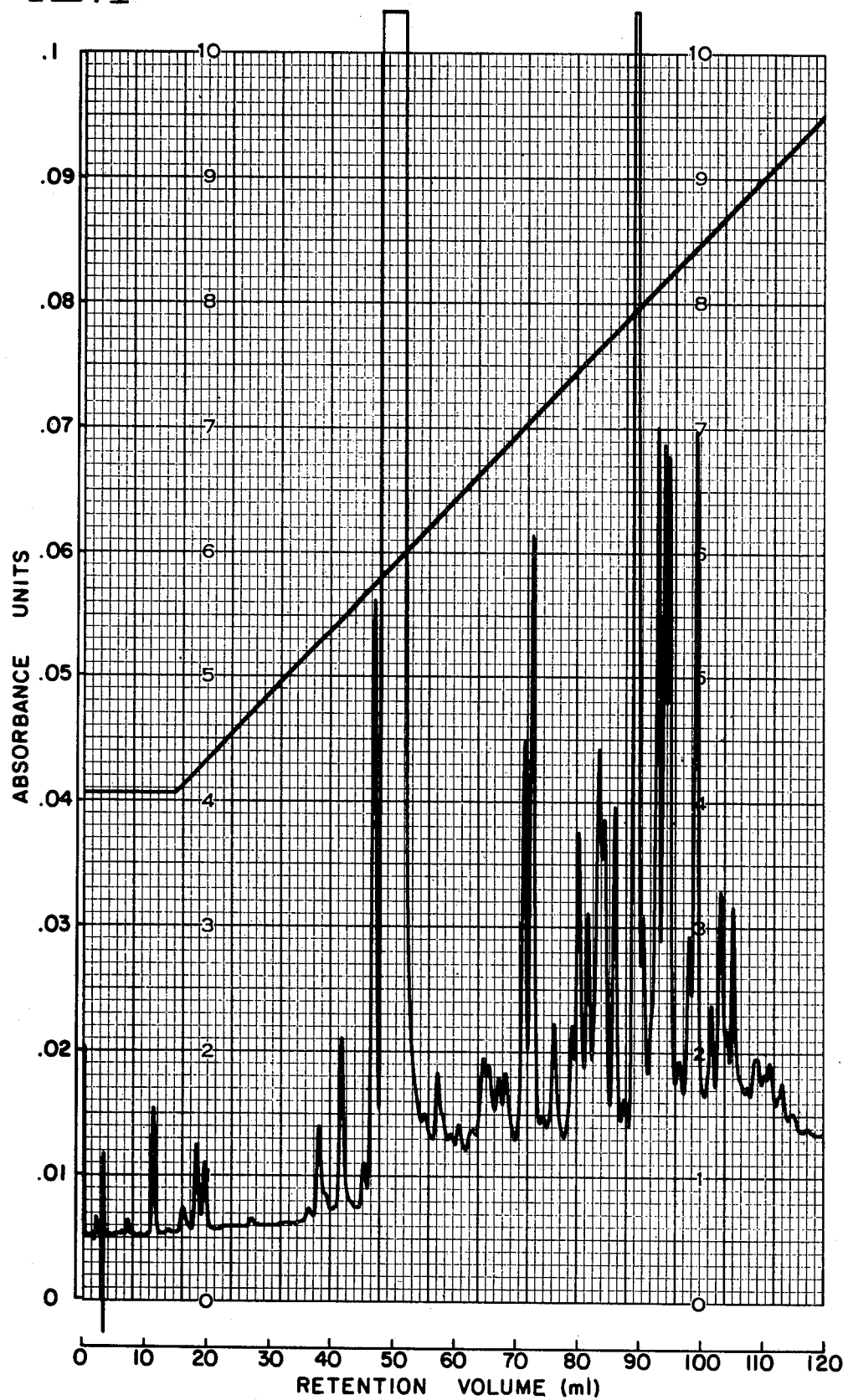

United States Patent [19]

Cleveland William K. S. et al.

[11] 4,391,996
[45] Jul. 5, 1983

[54] 1,1-DICHLORO-2,2-BIS(HYDROXYPHENYL)ETHYLENE

[75] Inventors: Cleveland William K. S., Amsterdam; Jimmy L. Webb, Ballston Lake; Charles M. Orlando, Glenville, all of N.Y.

[73] Assignee: General Electric Company, Schenectady, N.Y.

[21] Appl. No.: 321,644

[22] Filed: Nov. 16, 1981

Related U.S. Application Data

[60] Continuation-in-part of Ser. No. 117,727, Feb. 1, 1980, abandoned, which is a division of Ser. No. 919,461, Jun. 27, 1978, Pat. No. 4,221,901, which is a division of Ser. No. 765,654, Feb. 4, 1977, Pat. No. 4,117,018.

[51] Int. Cl.$^3$ ............................................. C07C 39/21
[52] U.S. Cl. .................................................... 568/726
[58] Field of Search ........................................ 568/726

[56] References Cited

U.S. PATENT DOCUMENTS 4,073,814  2/1978  Kinson et al. ......................... 560/57
4,110,541  8/1978  Kinson ................................. 568/725

OTHER PUBLICATIONS

Hubacher, Max P. *J. Organic Chemistry*, (1959) pp. 1949-1951.

*Primary Examiner*—Natalie Trousof
*Assistant Examiner*—L. Hendriksen
*Attorney, Agent, or Firm*—William A. Teoli; James C. Davis, Jr.; James Magee, Jr.

[57] ABSTRACT

A method is described for dehydrochlorinating 1,1,1-trichloro-2,2-bis(4-hydroxyphenyl)ethane employing a refluxing dipolar aprotic solvent, such as dimethylformamide, containing a lithium halide catalyst to produce a crystalline product consisting essentially of 1,1-dichloro-2,2-bis(4-hydroxyphenyl)ethylene. The crystalline product can be isolated in substantially pure form and converted to a high impact, flame retardant polycarbonate.

1 Claim, 3 Drawing Figures

1,1-DICHLORO-2,2-BIS(HYDROXYPHENYL-)ETHYLENE

CROSS REFERENCE TO RELATED APPLICATIONS

This application is a continuation-in-part of copending application Ser. No. 117,727, filed Feb. 1, 1980, now abandoned, which is a division of Ser. No. 919,461, filed June 27, 1978, now U.S. Pat. No. 4,221,901, which is a division of Ser. No. 765,654, filed Feb. 4, 1977 now U.S. Pat. No. 4,117,018.

BACKGROUND OF THE INVENTION

The present invention relates to a dehydrochlorination method based on the use of a dipolar aprotic solvent and a lithium halide under reflux conditions. More particularly, the present invention relates to the dehydrochlorination of 1,1,1-trichloro-2,2-bis(4-hydroxyphenyl)ethane to produce 1,1-dichloro-2,2-bis(4-hydroxyphenyl)ethylene.

As taught by S. Porejko and Z. Weilgosz, Synthesis and Properties of Polycarbonates with Chloro-bisphenols, Polymeri, 13 (2) 55 (1968) 1,1-dichloro-2,2-bis(4-hydroxyphenyl)ethylene of the formula,

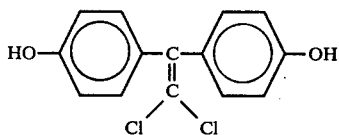

(1)

referred to hereinafter as "dichloride", can be used to make high molecular weight polycarbonate. The procedure recommended by Porejko et al for making the dichloride is based on the dehydrochlorination of the corresponding "trichloroethane dihydric phenol", or "trichloride", as shown by the following equation,

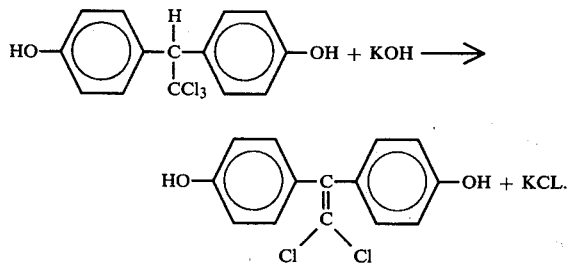

The trichloride, as taught by Porejko et al, can be made by a standard technique based on the condensation of chloral, or its hydrated form with phenol. As used hereinafter, the term "trichloride" will signify a trichloroethane bisphenol of the formula,

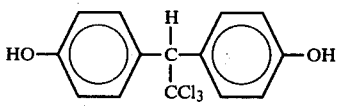

(2)

Experience has shown that although the preparation of trichloride by Porejko et al followed by its dehydrochlorination, using a methanol solution of potassium hydroxide, by the method of Porejko et al, can be employed to make dichloride, the resulting dehydrochlorination reaction solids can contain in addition to the dichloride, unreacted trichloride, and various contaminants. The following contaminants have been found in the trichloride dehydrochlorination reaction mixture of Porejko et al:

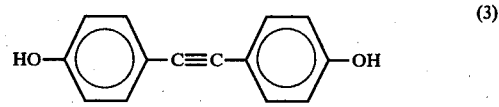

(3)

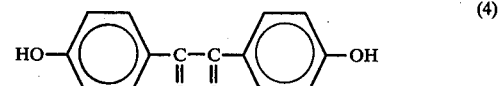

(4)

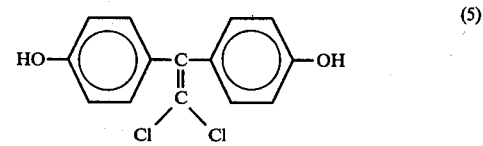

(5)

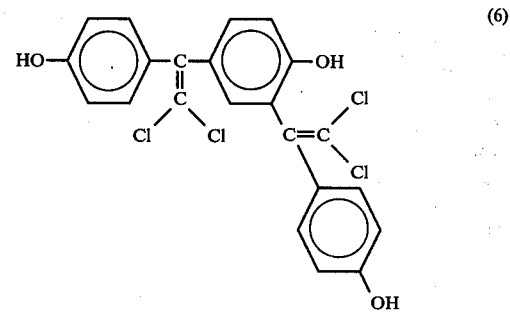

(6)

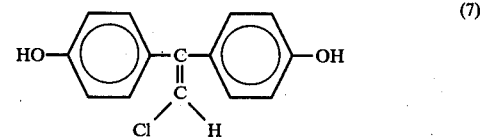

(7)

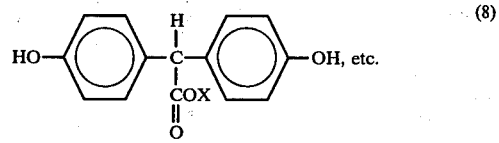

(8)

where X can be H or methyl.

FIG. 1 is a typical liquid chromatogram of a trichloride dehydrochlorination mixture made by Porejko et al. The dichloride absorbances of contaminants are also shown. Based on the use of a calibration curve obtained from using pure materials, the concentration of the trichloride having a retention volume of about 48 ml is about 3,200 ppm.

Figure 2:
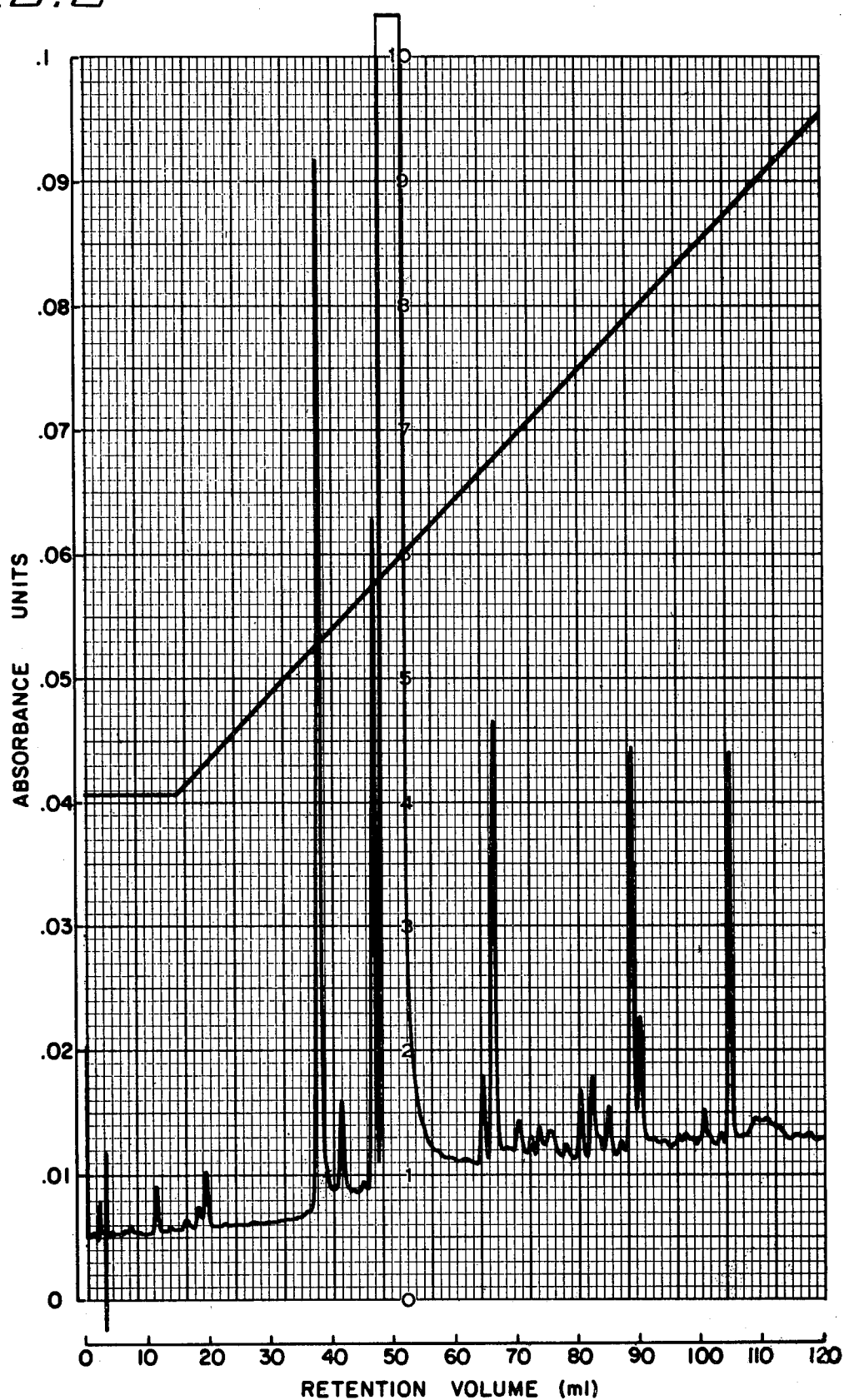

In Polish Pat. No. 144,756, Wielgosz et al taught that improved dichloride purity can be achieved, if 6–8 mols of KOH, per mol of trichloride instead of 15 mols of KOH per mol of trichloride is used for trichloride dehydrohalogenation. A temperature of 40°–50° C. is also recommended. However, FIG. 2, a liquid chromatogram of the dichloride made by Wielgosz et al's improved procedure still shows significant amounts of contaminants. The Wielgosz et al's dichloride has a dark color; it has an absorbance value of 1.24, as shown by measuring its absorbance in methanol solution (2.50 gm/50 ml in a 10 cm cell) using a Carey 14 recording spectrophotometer with light at 425 nm. In addition, as shown by FIG. 2, the trichloride concentration at 48 ml retention volume is about 3,600 ppm.

The present invention is based on the discovery that a more highly selective dehydrohalogenation of the trichloride can be achieved by the use of a refluxing dipolar aprotic solvent, such as dimethylformamide in the presence of a lithium halide catalyst, such as lithium chloride, followed by the addition of water to the reaction mixture to effect separation of substantially pure dichloride crystals. As used hereinafter, the expression "substantially pure" when referring to dichloride will signify a dichloride having an absorbance value of less than 0.3 when measured as described above. In addition, a substantially pure dichloride can provide a liquid chromatogram similar to FIG. 3, having less than 1000 ppm of trichloride which, except for dichloride, is substantially free of absorbances exceeding 60% and preferably 50% of the 0.1 AUFS (absorbance units full scale) when tested as follows:

A Waters Model 244 liquid chromatograph is used, equipped with a Model U6K injector, a $\mu$Bondapak $C_{18}$ column, a Model 440 detector equipped with a 10 mm cell and operated at 280 nm set at 0.1 AUFS and a 10 millivolt Houston Instrument Omniscribe recorder with a chart speed of 0.25 centimeters per minute. Ten microliters of 10% (wt/vol) methanol solution of the dichloride is injected into the column and it is eluted at 2 ml per minute, where the solvent mixture is programmed linearly over a 1 hour period from an initial composition of 40% methanol and 60% water to a final composition of 100% methanol.

Prior to the present invention, as shown by R. P. Holysz, JCS, 57 4432 (1353) dimethylformamidelithium chloride mixtures have been found to be effective for dehydrohalogenating fused ring systems for making 4-halo-3-keto steroids. More recently, O. R. Jackson et al, JCS, Perkin Trans II, 308 (1972) and McLellan et al, ibid, 1818 (1974), investigated the dehydrohalogenation of certain trichlorodiarylethanes using dimethylformamide and lithium chloride mixtures. Even though dimethylformamide and lithium chloride have been used to effect the removal of hydrogen chloride from various trichlorodiarylethanes, prior to the present invention such dehydrohalogenation was never attempted with a dihydric phenol, such as a trichloride of formula (2). Surprisingly, even though a significant degree of rearrangement would normally be expected, it has been found that only a minor amount of the dihydric phenol of formula (7) is generated during dehydrochlorination.

STATEMENT OF THE INVENTION

There is provided by the present invention, a method for making dichloride of formula (1) by dehydrochlorinating a trichloride of formula (2), which comprises, (A) refluxing a mixture containing as essential ingredients,
 (a) the trichloride,
 (b) a dipolar aprotic solvent,
 (c) a lithium halide, where there is used, per 100 parts by weight of (b), from 5 to 100 parts of (1) and 0.5 to 10 parts of (c), (B) adding water to the mixture of (A) at a temperature of from 120° C. to 70° C. to produce a mixture having from 100 to 150 parts of water, per 100 parts of dipolar aprotic solvent, (C) effecting the crystallization of dichloride from the resulting mixture of (B) at a temperature of from 70° C. to 25° C., and (D) recovering the dichloride from the mixture of (C).

Some of the dipolar aprotic solvent which can be used in the practice of the present invention are, for example, dimethylformamide, which is the preferred solvent, as well as dimethylacetamide, dimethylsulfoxide, N-methylpyrrolidone, etc. In addition to lithium chloride which can be employed from 1% to 10% by weight, based on weight of the trichloride, there also can be used other lithium salts, such as lithium bromide, lithium iodide, lithium carbonate, etc., and precursors to these salts.

In the practice of the invention, the dehydrochlorination of the trichloride can be achieved by dissolving the trichloride in a dipolar aprotic solvent, such as dimethylformamide, along with the required amounts of lithium halide as previously defined. Dehydrochlorination can be effected under an inert atmosphere, such as by employing nitrogen, etc. During the initial formation of the reaction mixture, the order of addition of the various ingredients is not critical.

Dehydrochlorination can be effected by heating the mixture to reflux, while it is being thoroughly agitated, such as by stirring. Depending upon the reflux temperature employed, the nature of the dipolar aprotic solvent, etc., dehydrochlorination can be effected over a period of from 1 to 24 hours.

Dehydrochlorination solids can be removed by allowing the reaction mixture to cool as defined above, and adding from 1.0 to 1.5 parts of water by weight, per part of dipolar aprotic solvent utilized in the dehydrochlorination mixture. The rate of addition of water to the mixture and optionally with external cooling is regulated to provide a mixture at a temperature of about 70° to 50° C., for example 65° C. The mixture can then be allowed to cool slowly under ambient conditions to allow for the crystallization of the dichloride of formula (1). The dichloride can then be slurried with additional water to remove residual dipolar aprotic solvent and thereafter dried at temperatures up to 90° C. to 110° C./10 mm.

In accordance with the practice of the present invention there is also provided a dichloride which is the dehydrochlorination reaction product of a trichloride of formula (2) having an absorbance value of less than 0.3, as shown by a Carey 14 recording spectrophotometer using 425 nm light as defined above and capable of providing a chromatogram substantially free of absorbance other than the dichloride of formula (1) which exceed 60% of 0.1 AUFS.

The above defined dichloride can be copolymerized with phosgene, carbon monoxide, or transesterfied with a diorgano carbonate, such as a dialkyl carbonate or diaryl carbonate to produce substantially color-free, flame retardant polycarbonate homopolymer. Methods for transesterification of polycarbonates are taught by Herman Schnell, Chemistry and Physics of Polycarbonates, interscience Publishers, John Wiley and Sons, New York (1964). Procedure for using carbon monoxide with Group VIIIB metal catalysts are taught in copending application of Allen Chalk, Ser. No. 731,496, filed Oct. 12, 1976 now U.S. Pat. No. 4,096,169 and assigned to the same assignee as the present invention.

There is also provided by the present invention, a polycarbonate homopolymer consisting essentially of chemically combined units of the formula,

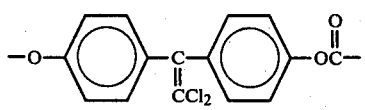

having a Notched Izod impact value of at least 15 ft-lbs/in, in accordance with ASTM test No. D256 Method A, which is the reaction product of a carbonyl precursor selected from the class consisting of carbon monoxide, phosgene and a diorganocarbonate and a dehydrochlorination reaction product of a trichloride of formula (2).

In order that those skilled in the art will be better able to practice the invention, the following examples are given by way of illustration and not by way of limitation. All parts are by weight.

EXAMPLE 1

There was charged to a reaction vessel, 1243 parts of sulfuric acid and 6.9 parts of glacial acetic acid. The mixture was cooled to 27° C. There was added 1190 parts of molten phenol to the mixture which was cooled to 20° C. There was added to the resulting mixture over a period of 7 hours, 622 parts of chloral while the temperature of the mixture was maintained between 18°-20° C. After stirring the mixture for 24 hours, there was added 1160 parts of water, resulting in the production of crude reaction product. A trichloride, as shown by formula (2), was recovered using a basket centrifuge.

The above trichloride was dissolved in a proportion of 1 part of trichloride to 2.18 parts of isopropanol. The isopropanol solution was heated to 50° C. while adding water to produce a 12% solids solution. The mixture was then allowed to cool to 20° C. over a two hour period. There was obtained an 82% yield of crystalline trichloride which was recovered with a basket centrifuge.

Following the procedure of Wielgosz et al, Polish Pat. No. 144,765, there was added 1.59 parts of the above trichloride to a solution of 1.68 part of potassium hydroxide and 3.12 parts of methanol, while maintaining the temperature of the resulting mixture at 40° C. The resulting mixture was agitated for 3 hours at 50° C. and then heated to reflux. The mixture was then allowed to cool and 3.5 parts of hydrochloric acid, having a concentration of 25% by weight of hydrogen chloride, was added to the mixture until it was neutral. The mixture was then heated to reflux and then allowed to cool to room temperature. The precipitate was collected on a scintered glass funnel, washed with water until the silver nitrate test for chloride was negative. The precipitate was then dried at a temperature of 100°-105° C. A temperature above 105° C., such as 120° C., as taught by Wielgosz et al, was not used to dry the dichloride since it was found to discolor the dichloride.

As previously indicated, the above dichloride made by the procedure of Wielgosz et al, Polish Pat. No. 144,765, was found to have an absorbance value of 1.24 using a Carey 14 spectrophotometer. In addition, the dichloride was found to have a dark color.

A liquid chromatogram was obtained for the Wielgosz et al dichloride using a Waters model 244 liquid chromatogram as previously described. The liquid chromatogram, as shown by FIG. 2, has a variety of unknown contaminants having absorbances of at least 0.06 or greater than 50% of 0.1 AUFS. In addition, as shown by FIG. 2, the dichloride had greater than 3,000 ppm of trichloride.

In accordance with the practice of the present invention, a solution of 2000 parts of the above trichloride in about 14,230 parts of dimethylformamide containing 120 parts of lithium chloride was heated with stirring for 5 hours at 151° C. The mixture was then allowed to cool to a temperature of between 90°-100° C., during which time there was added with stirring 20,000 parts of distilled water. The dilute mixture was then allowed to cool slowly over a period of about 8 hours to a temperature of 30° C. The resulting slurry was then further cooled to 20° C. and the mixture was then filtered. The solids were then washed with distilled water. There was obtained a 95% yield of the dichloride of formula (1).

The above dichloride was then dissolved in 4800 parts of dimethylformamide and the resulting solution was heated to 90° C. There was added to the dimethylformamide solution, an additional 6720 parts of water while the temperature was maintained at 80°-90° C. The mixture was then allowed to cool slowly at a rate of about 1° C. per minute. The slurry was then filtered and washed with additional distilled water.

Figure 3:
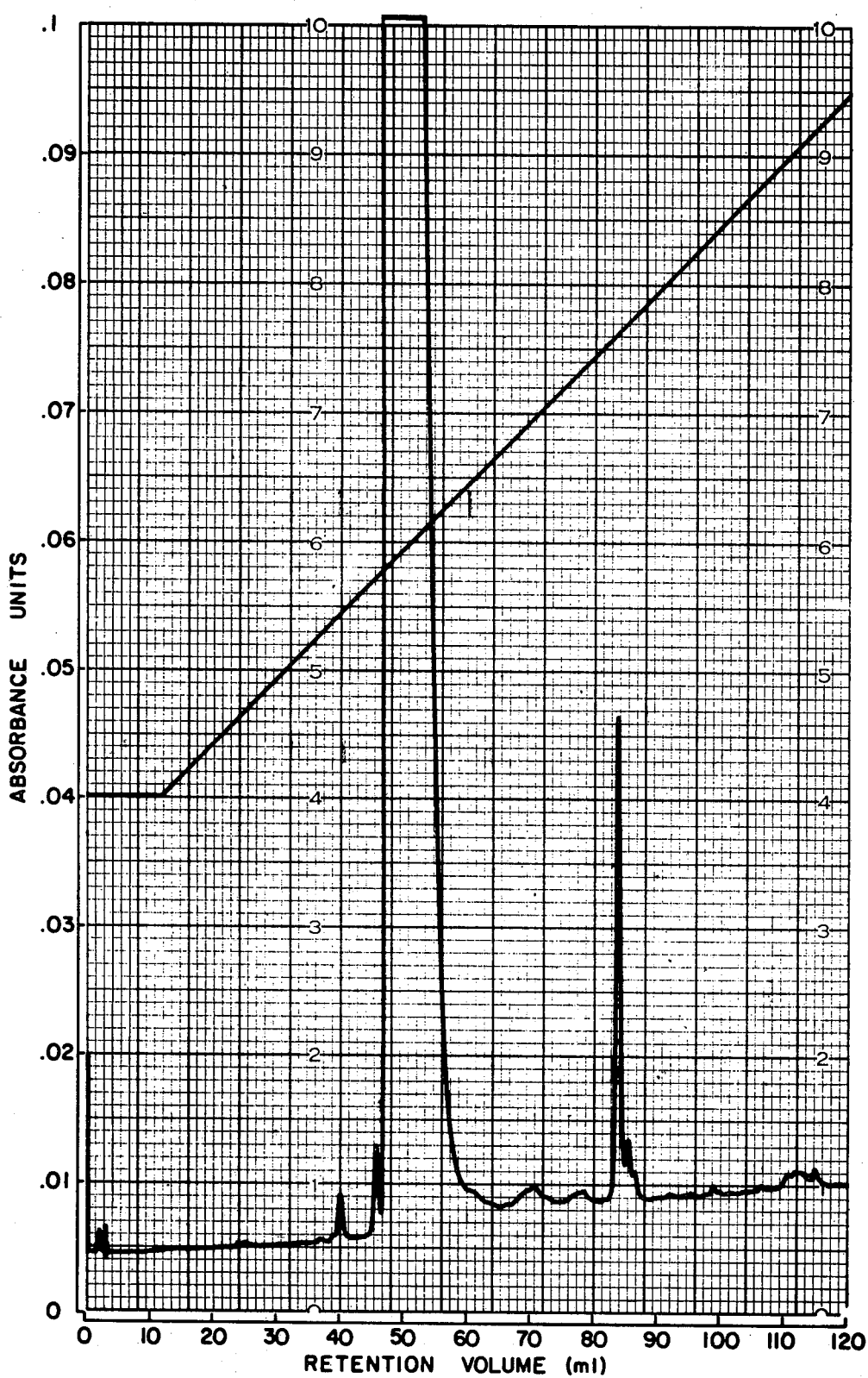

Following the same procedure, as utilized to determine the purity of the dichloride made by Wielgosz et al, the dichloride made in accordance with the practice of the present invention was substantially colorless. It was found to have an absorbance value of less than 0.3, using a Carey 14 recording spectrophotometer, employing a solution of 2.5 grams of the dichloride in 50 ml of methanol, a 10 centimeter cell and light at 425 nm. Following the same procedure with a liquid chromatogram as previously defined, there was obtained a liquid chromatogram as shown by FIG. 3. An examination of FIG. 3 shows that there are no absorbances other than the absorbance of the dichloride which exceeds 60% of 0.1 AUFS. In addition, there was found less than 1,000 ppm of trichloride and more particularly about 750 ppm of trichloride.

EXAMPLE 2

The dichloride of Example 1 of Wielgosz et al and the dichloride of the present invention, referred to as Cleveland et al, are respectively polymerized in accordance with a standard phosgenation technique as follows:

Phosgene is bubbled into the respective reaction mixtures over a period of 48 minutes at a rate of 0.52 to 1.63 parts per hour, consisting of 2.9 to 6.3 parts of water, 4.7 to 9.0 parts of dichloromethane, 1 part of dichloride, 0.008 part of phenol, 0.005 to 0.008 part of triethylamine and 0.002 part of sodium gluconate. During the introduction of the phosgene into the aforementioned mixture, the mixtures are agitated and maintained at a pH of about 11 to 11.5, employing a 50% aqueous sodium hydroxide solution. The mixtures become viscous and showed no further build in viscosity. The mixtures are then diluted with 2.9 to 4.3 parts of dichloromethane and the organic layers are separated from the aqueous phase. The organic layers are then washed with a 0.01 N aqueous hydrochloric acid then with water to produce a neutral resin solution. The polycarbonates are then isolated by removal of the solvent by steam precipitation according to procedures described by Niblett, Debacher and Wessel, U.S. Pat. No. 3,508,339. There are obtained polymers having intrinsic viscosities of 0.52 to 0.58 dl/g in methylene chloride at 25° C.

The chloroethylene polycarbonates of Wielgosz et al and Cleveland et al made by the above phosgenation procedure are processed into the appropriate test specimen for measurement of Notched Izod impact value in accordance with ASTM procedure D256 method a according to the following procedure:

The extrusions are done using a ¾ inch Brabender extruder, fitted with general purpose screw (compression ratio, 2:1) having a length/diameter ratio of 15:1. A 15° tip is used along with a ⅛ inch rod die. The temperature is maintained at 530° F. over the entire barrel. The screw speed is 100 rpm. The extrudates are air cooled and pelletized. The polymer powders are fed to the extruder throat resulting in an extrusion rate of about 3.8 pounds per hour and the torque is 1200 meter/gram.

The pellets of both polymer samples are dried in an air over at 125° C. for 3 hours. The dried pellets are molded on a 0.8 ounce Battenfeld injection molding machine with a screw speed of 80 rpm. The molding conditions are as follows: (1) Temperature—barrel set points, 570° F. and mold surface, 200° F. (2) Pressure—injection, 23,000 PSI and back pressure, minimum. (3) Cycle times—injection time/speed, 10 sec/fast; hold time, 15 sec.; open time, 2 sec.

It is found that the Notched Izod impact value of the chloroethylene polycarbonate based on the use of the dichloride made by the procedure of Wielgosz et al has a Notched Izod impact value of 2.95 ft-lb/in. The Notched Izod impact value of the chloroethylene polycarbonate resulting from the phosgenation of the dichloride of Cleveland et al has a Notched Izod impact value of 15.4 ft-lbs/in.

Dichloride also was made in accordance with the procedure of Max H. Hubacher, J. of Org. Chem., (1959) pages 1949–51, as follows:

A solution of 15.9 g of trichloride made in accordance with Example 1 of the present invention, in 100 ml 3 N methanolic potassium hydroxide, was refluxed for 30 minutes. After adding 300 ml ice water, the resulting purple solution was acidified. The precipitate was crystallized from 500–600 ml 80% ethanol as the crude product was found to be almost completely insoluble in 20% aqueous ethanol. There was obtained orange crystals having greater than 4,000 ppm of trichloride. Those skilled in the art would know, based on the results shown above, that the dichloride made by the Hubacher method would not be suitable for making high impact polycarbonate.

Although the above examples are directed to only a few of the very many variables which can be used in the practice of the method of the present invention, it should be understood that the present invention can employ a much broader variety of dipolar aprotic solvents, as previously indicated in the description preceding these examples, as well as other lithium halide salts to effect the dehydrochlorination of the trichloride of formula 2.

The chloroethylene polycarbonates made in accordance with the practice of the present invention can be injection molded to a variety of useful high impact parts and shapes similar to the molding of Lexan polycarbonate.

Other procedures for effecting the removal of contaminants from trichloride dehydrochlorination reaction products are shown by Philip L. Kinson in application Ser. No. 767,045, filed Feb. 9, 1977, now abandoned and U.S. Pat. No. 4,110,541 and Kinson et al U.S. Pat. No. 4,073,814, all assigned to the same assignee as the present invention.

What we claim as new and desire to secure by Letters Patent of the United States is:

1. A dichloride of the formula,

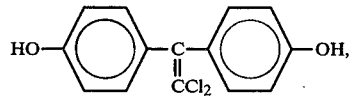

which has a trichloride impurity of the formula

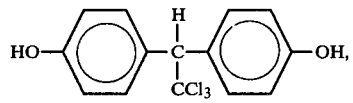

which is present in said dichloride at a concentration of less than about 1000 ppm.

* * * * *